US008900276B2

(12) United States Patent
Purcell et al.

(10) Patent No.: US 8,900,276 B2
(45) Date of Patent: Dec. 2, 2014

(54) ADJUSTABLE OCCIPITAL PLATE

(75) Inventors: Thomas Purcell, Del Mar, CA (US);
Frank Eismont, Miami, FL (US)

(73) Assignee: Alphatec Spine, Inc., Carlsbad, CA (US)

( * ) Notice: Subject to any disclaimer, the term of this patent is extended or adjusted under 35 U.S.C. 154(b) by 1747 days.

(21) Appl. No.: 11/544,889

(22) Filed: Oct. 6, 2006

(65) Prior Publication Data

US 2007/0118121 A1    May 24, 2007

Related U.S. Application Data

(60) Provisional application No. 60/724,962, filed on Oct. 7, 2005.

(51) Int. Cl.
A61F 2/30    (2006.01)
A61B 17/70    (2006.01)

(52) U.S. Cl.
CPC ................... *A61B 17/7055* (2013.01)
USPC ........................................................ 606/280

(58) Field of Classification Search
USPC ........... 606/54, 59, 60, 61, 69, 70, 71, 72, 73, 606/246–279, 281–299, 300–331
See application file for complete search history.

(56) References Cited

U.S. PATENT DOCUMENTS

| 4,905,680 | A | * | 3/1990 | Tunc | 606/280 |
| 5,084,049 | A | * | 1/1992 | Asher et al. | 606/251 |
| 5,368,594 | A | * | 11/1994 | Martin et al. | 606/252 |
| 5,545,164 | A | * | 8/1996 | Howland | 606/250 |
| 6,620,164 | B2 | * | 9/2003 | Ueyama et al. | 606/261 |
| 7,232,441 | B2 | * | 6/2007 | Altarac et al. | 606/250 |
| 2002/0049446 | A1 | * | 4/2002 | Harkey et al. | 606/70 |
| 2003/0176864 | A1 | * | 9/2003 | Ueyama et al. | 606/61 |
| 2004/0153070 | A1 | * | 8/2004 | Barker et al. | 606/61 |
| 2005/0124994 | A1 | * | 6/2005 | Berger et al. | 606/61 |
| 2006/0217710 | A1 | * | 9/2006 | Abdou | 606/54 |
| 2006/0235411 | A1 | * | 10/2006 | Blain et al. | 606/72 |
| 2007/0049932 | A1 | * | 3/2007 | Richelsoph et al. | 606/61 |
| 2007/0118121 | A1 | * | 5/2007 | Purcell et al. | 606/61 |
| 2008/0051783 | A1 | * | 2/2008 | Null et al. | 606/61 |
| 2009/0270924 | A1 | * | 10/2009 | Wing et al. | 606/280 |

FOREIGN PATENT DOCUMENTS

WO    WO 95/31147    11/1995

OTHER PUBLICATIONS

International Search Report No. PCT/US2006/039549, date of mailing Mar. 5, 2007.

* cited by examiner

*Primary Examiner* — Christopher Beccia

(74) *Attorney, Agent, or Firm* — Michael J. Loi

(57) ABSTRACT

Embodiments of an adjustable occipital plate is provided. The plate includes a fixation plate, at least one lateral rod configured to be coupled to the fixation plate, at least one sliding link configured to be coupled to the at least one lateral rod, and at least one posterior cervical rod configured to be coupled to the at least one sliding link using at least one rod connector.

45 Claims, 10 Drawing Sheets

ADJUSTABLE OCCIPITAL PLATE

CROSS-REFERENCE TO RELATED APPLICATIONS

The present application claims priority to U.S. Provisional Application No. 60/724,962, to Purcell, filed Oct. 7, 2005, and titled "Adjustable Occipital Plate" and incorporates its entire disclosure hereby by reference.

BACKGROUND OF THE INVENTION

1. Field of the Invention

The present invention relates generally to the field of surgery, and more specifically, to an adjustable occipital plate which may be used in conjunction with a posterior rod system to fixate the occipital/cervical junction between the cranium and the spine.

2. Background of the Invention

Occipito-cervical fixation has been achieved using a variety of techniques which generally provide stabilization of the base of the skull with respect to the neck. In order to promote fusion, for example, bone struts formed of autogenous ribs or curved iliac crest struts have been fixed to the occiput and spinous processes, cervical laminae, or facets. Wires are used to fix the struts in place until bone fusion occurs.

The thickness of the occiput varies, however, and thus, the occiput is typically wired in regions of greater thickness such as near the foramen magnum, at the nuchal line, and along the midline crest. Holes are drilled in the occiput to receive the wires that are also fed through holes in the struts. Although bone fusion occurs with this technique, the struts may be weak prior to fusion, and additional orthosis is applied such as with a halo vest or other hard collar until the struts can provide acceptably strong immobilization. Alternatively, metal struts may be used.

Other techniques for occipito-cervical fixation involve the use of other metal implants. One metal implant is a stainless steel, U-shaped device known as a Steinman pin. The threaded pin is bent to match the contour of the occipito-cervical region, and fixed to the occiput and cervical laminae or facets using wires. The pin is generally symmetrically disposed about the spine, with the sides of the "U" creating a central region in which a bone graft can be disposed and further wired to the pin. When attached to the occiput and spine, the pin assumes an inverted-U configuration. Several holes are formed in the occiput so that the U-bend may be fixed in place.

Additional metal implants include grooved or roughened titanium rods, smooth steel rods in the form of a Hartshill rectangle or Ransford loop, a Cotrel-Dubousset rod screw plate, and titanium frames have been employed.

SUMMARY OF THE INVENTION

Embodiments of the present invention are directed to an adjustable occipital plate for fixating the occipital/cervical junction between cranium and the spine. Some embodiments of the present invention use a variety of components to achieve a range of motion in several different axes. This extended range of motion allows the plate to adapt to the surrounding anatomy as well as making it more facile to adapt to a posterior rod fixation system.

In one embodiment, an adjustable occipital plate is presented which includes a fixation plate, at least one lateral rod configured to be coupled to the fixation plate, at least one sliding link configured to be coupled to the at least one lateral rod, and at least one posterior cervical rod configured to be coupled to the at least one sliding link using at least one rod connector.

In another embodiment, an adjustable occipital plate is presented which includes a fixation plate, two lateral rods configured to be coupled to the fixation plate, two sliding links, each configured to be coupled to each of the two lateral rods, and two posterior cervical rods, each configured to be coupled to each of the two sliding links using rod two connectors.

In another embodiment, a method of assembling an adjustable occipital plate is presented which includes providing a fixation plate and at least one lateral rod, slidably coupling at least one sliding link to the at least one lateral rod, connecting the fixation plate to the at least one lateral rod, and coupling at least one posterior cervical rod to the at least one sliding link using at least one rod connector.

In some embodiments, the components of the adjustable occipital plate may be initially variable and free to move, but may also be locked in a static position once correct placement is achieved in a patient.

The fixation plate may be a bone plate that includes a configuration of one or more (or a plurality) openings for receiving bone screws. The plate may also include attachment points for lateral rods. The lateral rods may be attached to the fixation plate and may extend laterally from the midpoint of the plate. Accordingly, the rods are used to achieve rotation and translation with the corresponding sliding links.

The sliding links may be used as a connector between the lateral rods, rod connector, and cervical rods. Such links may be free to move laterally and/or rotationally, and may be compressed to lock statically with the torque of the setscrew.

The rod connectors may be connected to the sliding links and may be held in place with a washer. To that end, the rod connectors may receive the posterior cervical rod as well as a setscrew (the setscrews may be the actuating mechanism that locks the entire assembly).

Further embodiments, features, objects and advantages of the invention, as well as structure and operation of various embodiments of the invention, are disclosed in detail below with references to the accompanying drawings.

BRIEF DESCRIPTION OF THE DRAWINGS

The present invention is described with reference to the accompanying drawings. Like reference numbers appearing in the figures indicate identical or functionally similar elements. Additionally, the left-most digit(s) of a reference number identifies the drawing in which the reference number first appears.

DETAILED DESCRIPTION OF THE INVENTION

Figure 1:
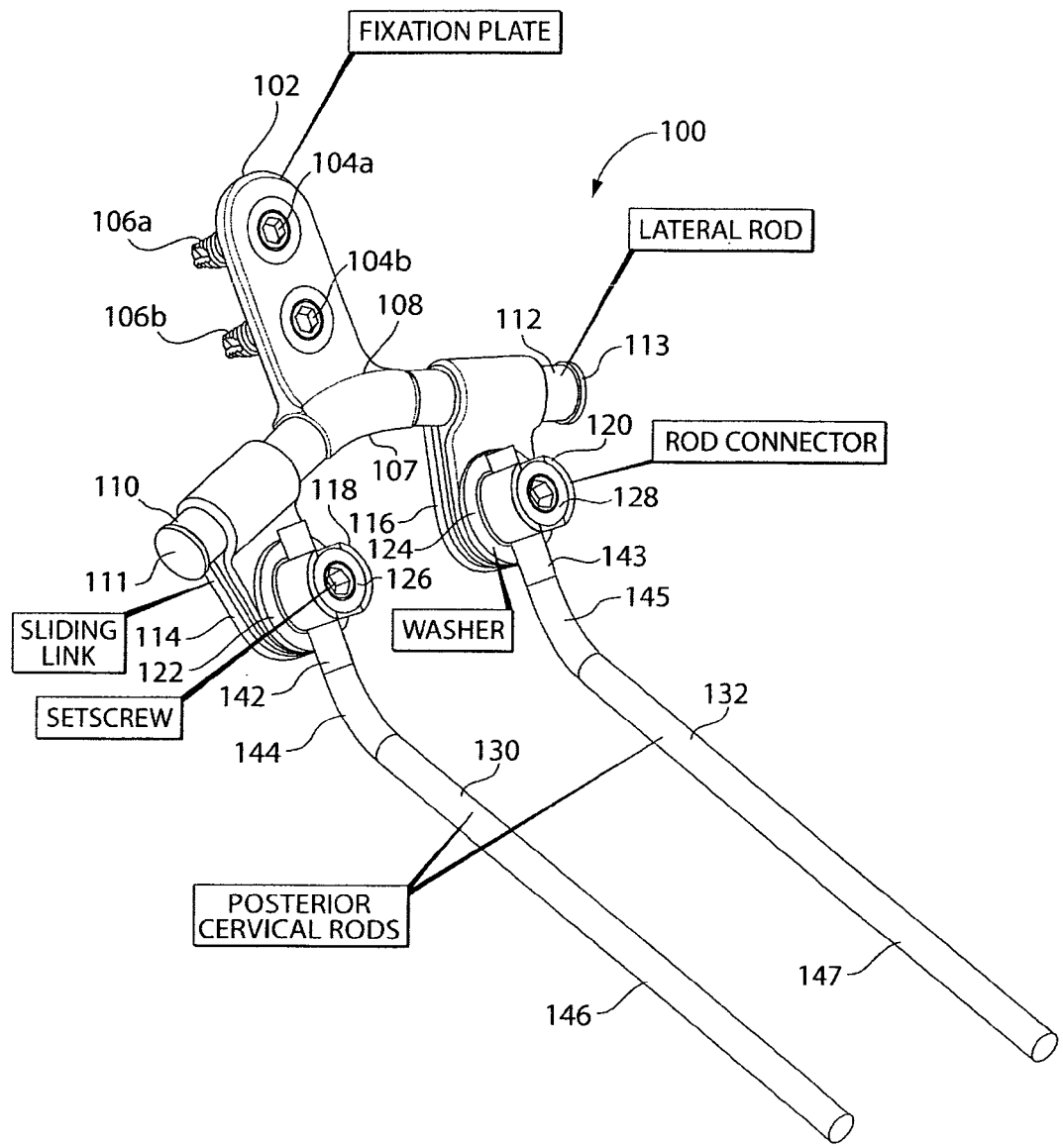
FIG. 1 illustrates an exemplary embodiment of an adjustable occipital plate, according to the present invention.

As shown in FIGS. 1-4, which illustrate exemplary embodiments of such an adjustable occipital plate according to the present invention, adjustable occipital plate 100 includes a fixation plate 102, a lateral rod 108, a first sliding link 114, a second sliding link 116, a first rod connector 118, a second rod connector 120, a first posterior cervical rod 130, and a second posterior cervical rod 132.

According to some embodiments, the lateral rod 108 may include a middle portion 107, a first end 110, and a second end 112, with the middle portion 107 being located between the first end 110 and the second end 112. In some embodiments, the fixation plate 102 may also incorporate middle portion 107, and the middle portion may also be integral with or coupled to the two lateral rods 110, 112. In the following description, the terms "first and second ends 110, 112" and "first and second lateral rods 110, 112" are used interchangeably. As can be understood by one skilled in the art, other embodiments of the lateral rod 108 are possible.

The angle of the middle portion 107 can be variable, depending on a setting desired for a particular patient. The first end 110 may also include a stopper 111 configured to prevent sliding link 114 from sliding away from the lateral rod 108. The second end 112 may also include a stopper 113 configured to prevent sliding link 112 from sliding away from the lateral rod 108. In some embodiments, the fixation plate 102 may be coupled to the middle portion 107 of the lateral rod 108. The fixation plate 102 may be coupled to the middle portion 107 in a way so it is symmetrically placed with respect to the two ends 110 and 112. In an embodiment, the fixation plate 102 can be glued, welded, screwed, or attached by any other means to the lateral rod 108 (or the lateral rods 110, 112). In an alternate embodiment, the fixation plate 102 and the lateral rod 108 can be an integral structure. In yet another alternate embodiment, the fixation plate 102 and the ends 110, 112 can be separate structures that are coupled together to form a fixation plate 102 and lateral rod 108 structure as shown in FIG. 1. As can be understood by one skilled in the art, other embodiments of the fixation plate 102 and the lateral rod 108 are also possible.

Figure 4:
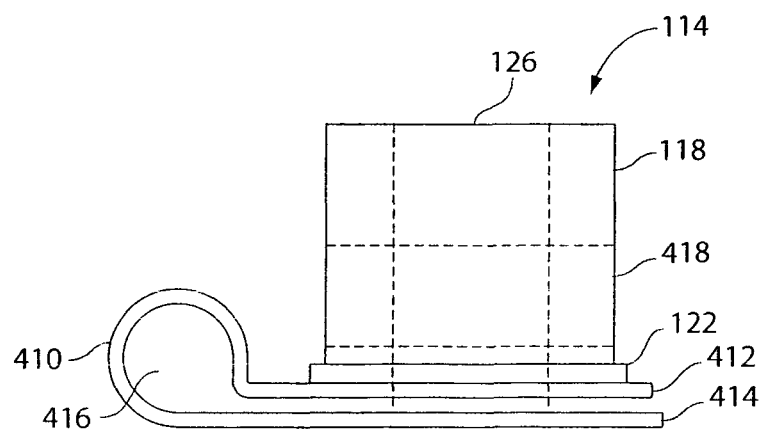
FIG. 4 is another side view the exemplary sliding link along with rod connector, according to the present invention.

The first sliding link 114 may be configured to be secured to the first end 110 of the lateral rod 108. As shown in FIG. 4, the first sliding link 114 includes a top portion 412 and a bottom portion 414, coupled to each other by a round portion 410. In one embodiment, each of the portions 410, 412, 414 has a substantially uniform thickness. As can be understood by one skilled in the art, the thicknesses can be variable.

The top and bottom portions 412, 414 are preferably substantially parallel and adjacent to each other, as shown in FIG. 4. The round portion 410 may include a hollow interior 416 configured to accommodate the first end 110 (not shown in FIG. 4). The top and bottom portions 412, 414 can be pushed closer together using the setscrew 126 located in the rod connector 118. Once the portions 412, 414 are pushed together, the round portion 410 compresses, thus, decreasing the diameter of the hollow interior 416. Once the round portion 410 is compressed, it creates a friction fit coupling with the first end 110 (not shown in FIG. 4). The frictional fit prevents the first sliding link from translation and rotation movements about the first end 110. To prevent further slippage and provide additional support, a washer 122 may be placed between the rod connector 118 and the top portion 412 of the first sliding link 114.

The rod connector 118 may also include a tunnel opening 418 that extends substantially parallel to the top and bottom portions 412, 414. The tunnel opening 418 is configured to accommodate insertion of the first posterior cervical rod 130 (not shown in FIG. 4). In one embodiment, the tunnel opening 418 can extend through the first rod connector 118 and setscrew 126. In this way, upon the first posterior cervical rod 130 being inserted through the tunnel opening 418, both ends of rod 130 can extend beyond the rod connector 118, as shown in FIGS. 1 and 2.

Figure 2:
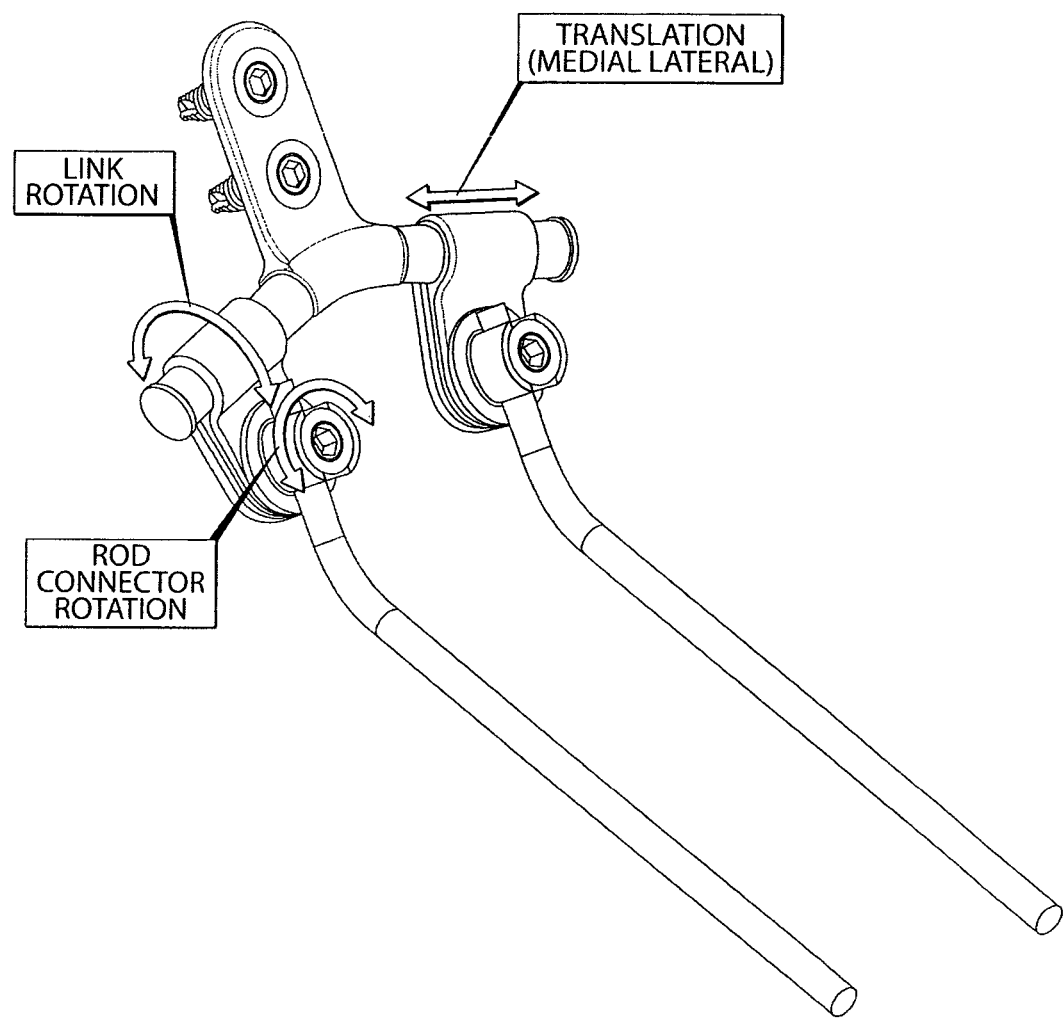
FIG. 2 illustrates another exemplary embodiment of an adjustable occipital plate, according to the present invention.
Figure 3:
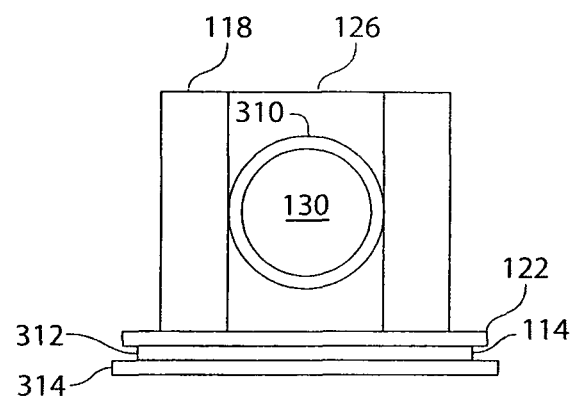
FIG. 3 is a side view of an exemplary sliding link along with rod connector, according to the present invention.

FIG. 3 is another side view of the rod connector 118, illustrating an opening 310 located on an exterior surface of the rod connector 118. The opening 310 serves to accommodate insertion of the posterior cervical rod 130. Once the rod 130 is inserted into the opening 310, it is pushed through the tunnel opening 418 (not shown in FIG. 3). Once pushed through the tunnel opening 418, the rod 130 protrudes through an opening in the rod connector 118, similar to the opening 310, located on the exterior of the rod connector 118 and opposite to the opening 310 (as shown in FIGS. 1 and 2). FIG. 3 further illustrates top and bottom portions 312 and 314 of the sliding link 114, which are similar to portions 412 and 414 (FIG. 4), respectively. The cervical rod 130 may be secured to the sliding link 114 by tightening the setscrew 126. In one embodiment, the setscrew 126 may also be statically secure sliding link 114 to the first end 110.

The first rod connector 108 may be configured to rotate about an axis that is substantially perpendicular to the top portion 412, as shown in FIG. 2. By rotating the first rod connector 108, a position and an orientation of the first posterior cervical rod 130 can be adjusted. This enables a surgeon to custom fit the adjustable occipital plate 100 to a particular patient. The setscrew 126 may statically secure the rod connector 108 to the sliding link 114.

The first sliding link 114 may be configured to rotate about the first end 110, as shown in FIG. 2. In an alternate embodiment, the first sliding link 114 may be configured to translate along the first end 110, as is also shown in FIG. 2. The first sliding link 114 may be translated between stopper 111 and the point where the fixation plate 102 couples to the first end 110. This type of translation may be referred to as medial lateral translation.

The above-referenced translations and rotations allow a surgeon to custom-fit the occipital plate to a patient in accordance with patient's physiological characteristics and needs.

Referring back to FIG. 1, the fixation plate 102 includes two openings 104a and 104b, configured to accommodate screws 106a and 106b, respectively. Screws 106 can be cervical screws or any other type of bone screws or attachment/fastening means/devices. As can be understood by one skilled in the art, the fixation plate 102 may include at least one opening 104, where each opening 104 accommodates a screw 106. The fixation plate 102, along with the screw(s) 106, allows attachment of the occipital plate 100 to bone in the neck region of the patient.

As shown in FIGS. 1 and 2, the posterior cervical rod 130 includes a rod connector attachment section 142, a curved section 144, and an elongated section 146. The rod connector attachment section 142 is configured to be inserted into the rod connector 118. The curved section 144 has a curvature that can be selected based on specific patient's physiological characteristics (though the curved section may be replaced by an angled section). The curved section 144 couples to the connector attachment section 142. The elongated section 146 couples to the curved section 144 and is configured to be inserted into patient's cranium region. The elongated section 146 may have a variable length that can be selected based on specific patient's physiological characteristics. As can be understood by one skilled in the art, similar situations exist with regard to the second posterior cervical rod 132.

As can also be understood by one skilled in the art, the above description with regard to the first sliding link 114 is equally applicable to the second sliding link 116.

Figure 6:
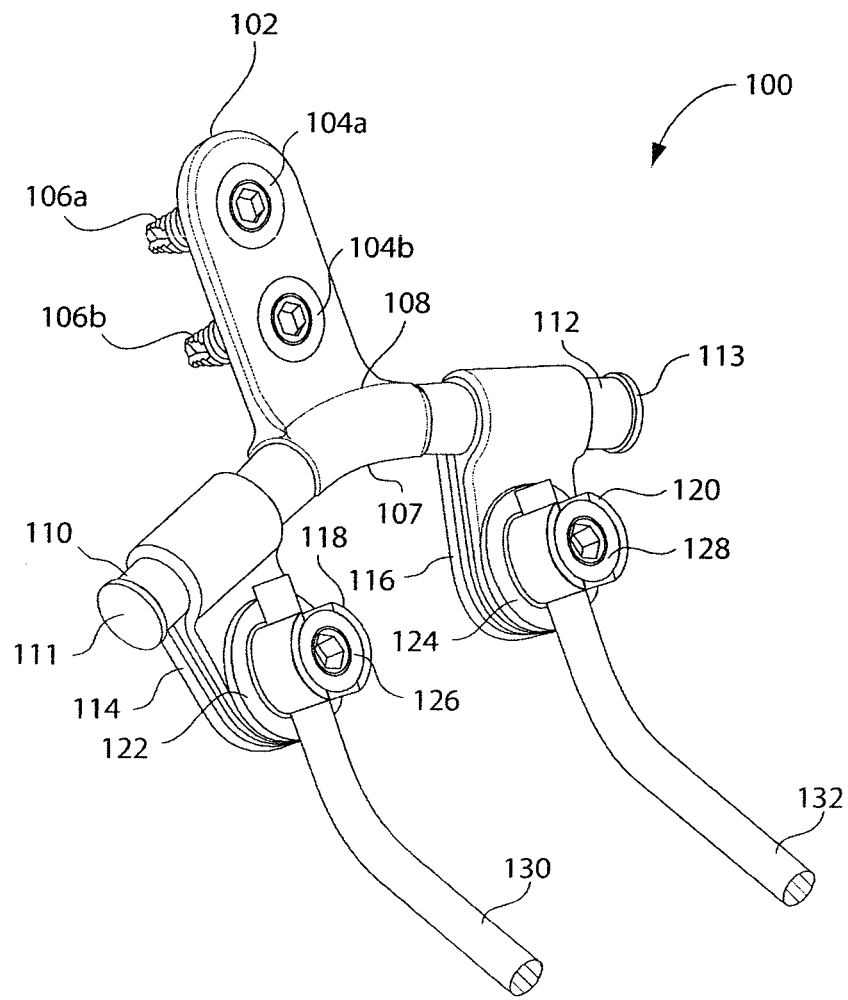
FIG. 6 is an enlarged perspective view of the exemplary adjustable occipital plate illustrated in FIG. 1.

FIG. 6 is an enlarged perspective view of a portion of the adjustable occipital plate 100 illustrated in FIGS. 1-4. As illustrated, the plate 100 includes the fixation plate 102, rods 110, 112, sliding links 114, 116, rod connectors 118, 120, setscrews 126, 128, and cervical rods 130, 132. As discussed above with respect to FIGS. 1-4, the adjustable occipital plate 100 is configured to secure at least one cervical rod 130 (or 132) and thereby connect portions of the patient's neck and cranium.

Figure 8:
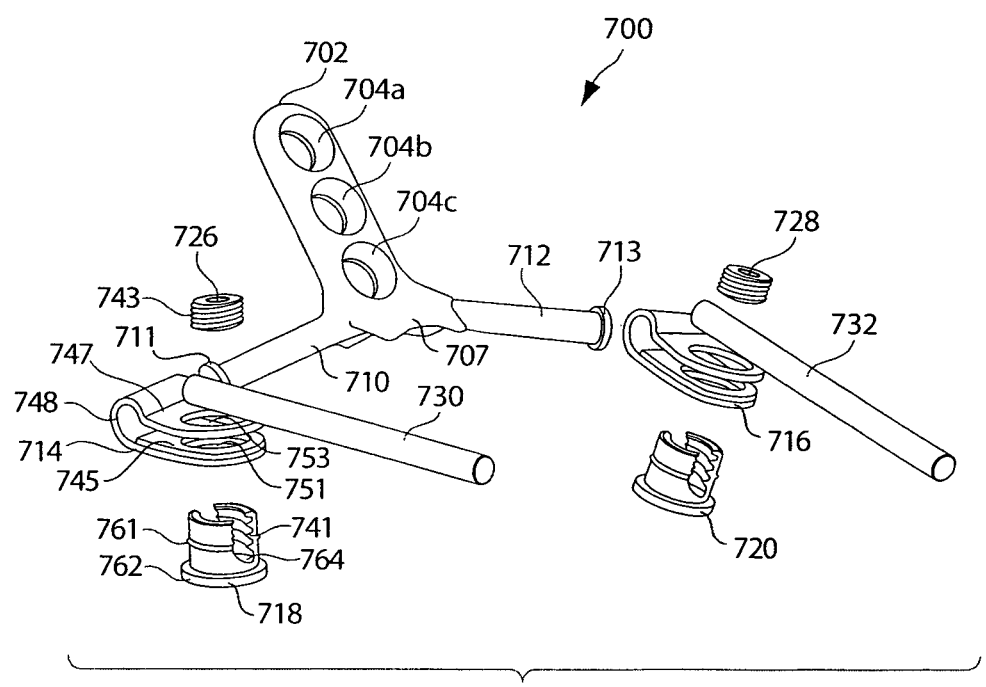
FIG. 8 is an exploded view of the embodiment of the exemplary adjustable occipital plate illustrated in FIG. 7.
Figure 9:
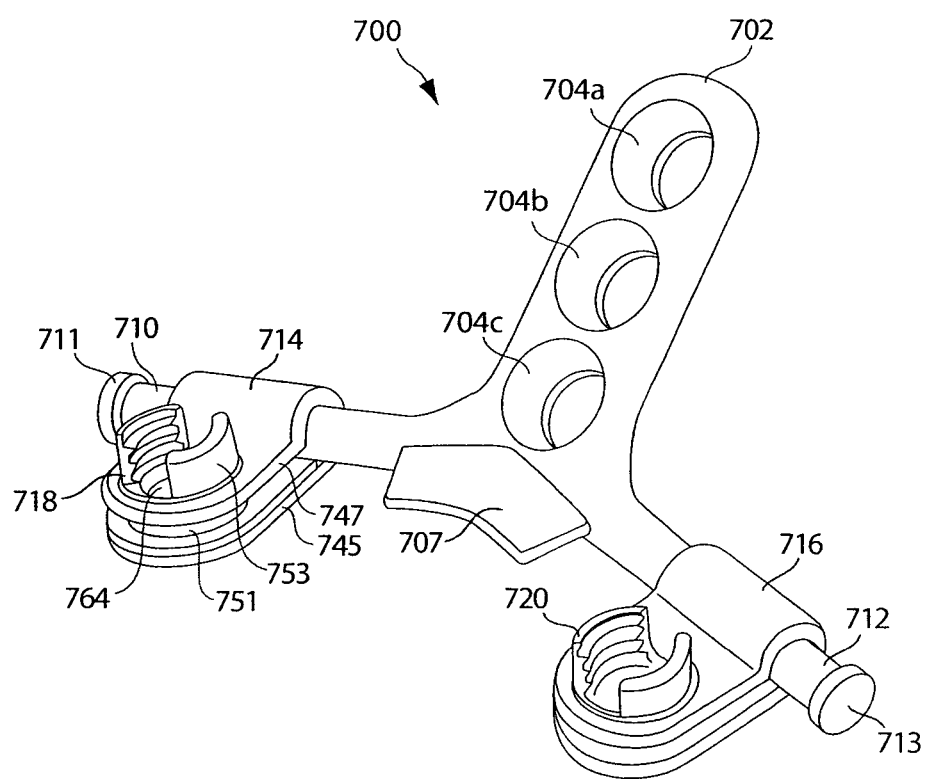
FIG. 9 is an enlarged perspective view of a portion of the exemplary adjustable occipital plate illustrated in FIG. 7.
Figure 10:
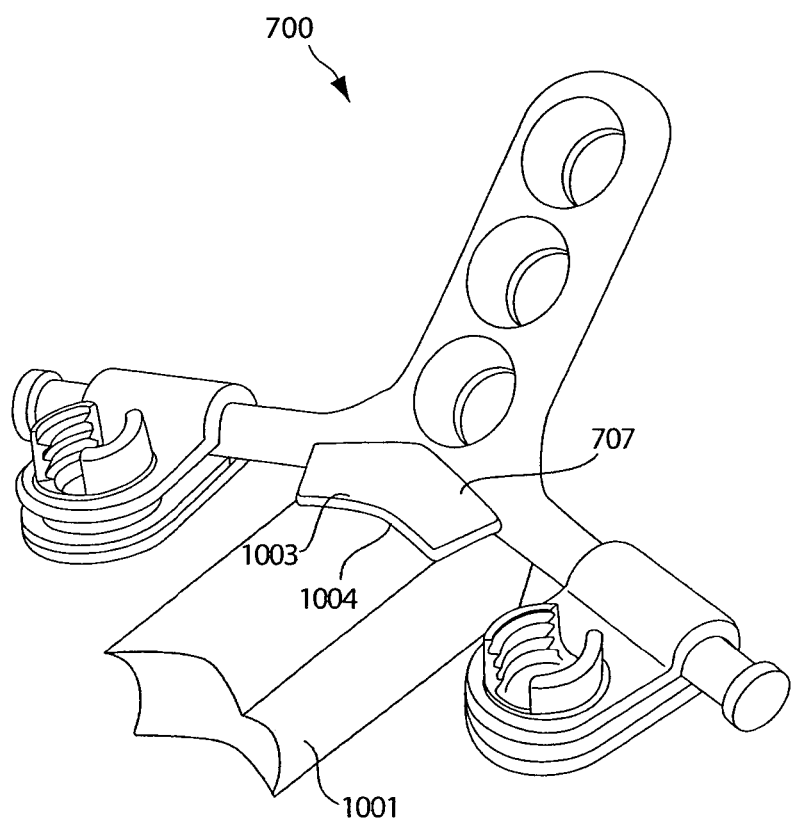
FIG. 10 is an enlarged perspective view of a portion of the exemplary adjustable occipital plate illustrated in FIG. 7 that includes a bone graft portion.

Another embodiment of an adjustable occipital plate is illustrated in FIGS. 7-10. As shown, an adjustable occipital plate 700 includes a fixation plate 702, lateral rods 710, 712, a first sliding link 714, a second sliding link 716, a first rod connector 718, a second rod connector 720, a first posterior cervical rod 730, and a second posterior cervical rod 732. The fixation plate 702 includes a middle portion 707 to which the first lateral rod 710 and the second lateral rod 712 are coupled. When the plate 700 is assembled, the middle portion 707 is located between the first lateral rod 710 and the second lateral rod 712. FIG. 10 illustrates the adjustable occipital plate in combination with a bone graft.

The fixation plate 702 can be integral to rods 710, 712 (e.g., unitary structure) or may be attached to the rods by means of welding, gluing, soldering, a locking mechanism, and the like. The angle of the middle portion 707 can be variable, depending on a setting desired for a particular patient. The first rod 710 may also include a stopper 711 that is configured to prevent sliding link 714 from sliding away from the rod 710. The second rod 712 may also include a stopper 713 that is configured to prevent sliding link 716 from sliding away from the rod 712. The fixation plate 702 can be placed symmetrically with respect to the two rods 710 and 712.

The first sliding link 714 may be configured to be secured to the first rod 710 in a fashion similar to one shown in FIG. 4. As shown in FIG. 8, the first sliding link 714 includes a top portion 747 and a bottom portion 745. The top and bottom portions 747, 745 are substantially parallel to each other and may be attached to each other using a curved portion 748. The curved portion 748 has a diameter that is substantially equal to or slightly greater (or, in some cases, smaller) than the diameter of the first rod 710, prior to threading and tightening setscrews 726 and 728. This way, the curved portion 748 can be placed over the first rod 710 and thereby allows translational and rotational movement of the sliding link 714 (as discussed in FIGS. 1-4) along the first rod 710 when the sliding link 714 is not secured to first rod 710.

The top and bottom portions 747, 745 further include openings 753, 751, respectively. The openings 753 and 751 may configured to allow placement of the first rod connector 718. The openings 753, 751 may be circular, though, as can be understood by one skilled in the art, these openings can have any other shape.

The first rod connector 718 includes a top portion 761 and a base portion 762, with the base portion 762 having a greater diameter than the top portion 761. The top portion and the base portion may be circular, though, as can be understood by one skilled in the art, these portions can have any other shape. The top portion 761 further includes a channel 764 configured to have a width that is substantially equal to or slightly greater than the diameter of the posterior cervical rod 730. In this way, the cervical rod 730 can be accommodated by the first rod connector 718. The channel 764 is preferably configured to have a depth that is substantially equal to or slightly greater than a combination of the height of the setscrew 726 and the diameter of the cervical rod 730. This allows the setscrew 726 to secure the cervical rod 730, when the cervical rod 730 is placed in the channel 764.

The channel 764 may be further configured to have a threading 741 on its inner walls. The setscrew 726 is configured to have a threading 743. The threading 741 and threading 743 are configured to interact with each other, when the setscrew 726 is inserted into the channel 764 to secure the cervical rod 730.

To secure the cervical rod 730, the top portion 761 of the rod connector 718 is first inserted through the opening 751 of the bottom portion 745 of the first sliding link 714 and then the top portion 761 is inserted through the opening 753 of the top potion 747 of the sliding link 714. The top portion 761 is inserted until the base portion 762 contacts the bottom portion 745 of the sliding link 714. Once this occurs, the base portion 762 prevents any further movement through the openings 751, 753. FIG. 9 is a perspective view of a portion of the adjustable occipital plate 700 that illustrates rod connectors 718, 720 placed through the openings 751 and 753 of the sliding links 714, 716.

The cervical rod 730 may then be placed inside the channel 764 and the setscrew 726 threaded along threads 741 of the channel 764 to secure the cervical rod 730. By advancing the setscrew 726 along the threads 741, the top and bottom portions 747, 745 are forced together (i.e., the base portion 762 and the cervical rod 730 are brought together). Once the portions 747, 745 are forced together, the curved portion 748 of the sliding link 714 securely grips the lateral rod 708 and fixes (or friction fits) the sliding link 714 to the lateral rod 708.

Figure 7:
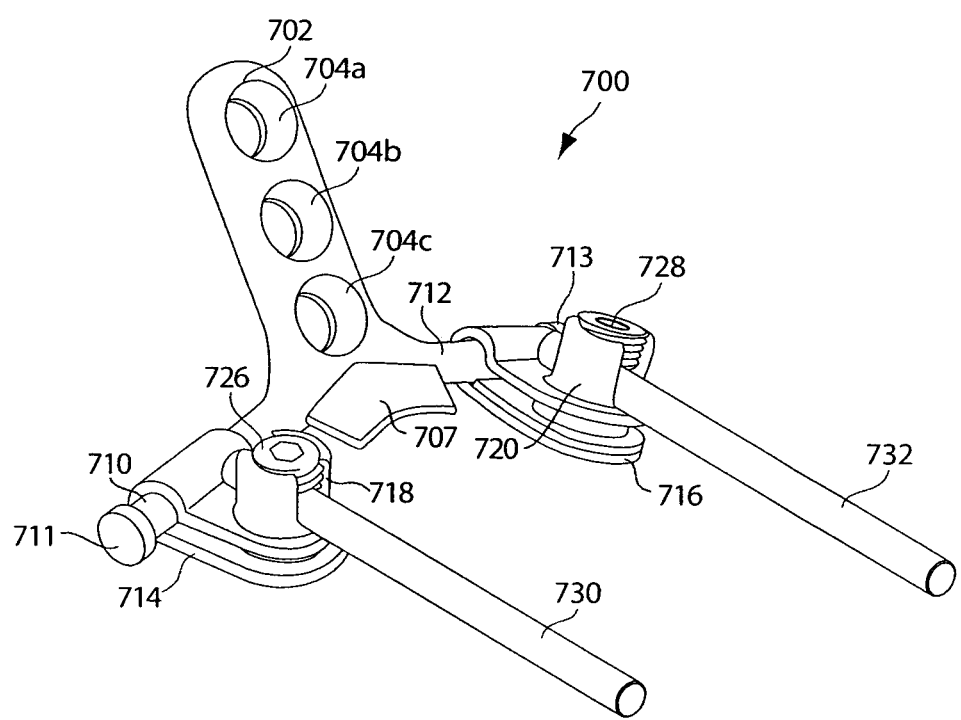
FIG. 7 is a perspective view of another embodiment of an exemplary adjustable occipital plate, according to the present invention.

As can be understood by one skilled in the art, the above description of the first sliding link 714, the first rod connector 718, the first setscrew 726, and the first posterior cervical rod 730 is also applicable to the second sliding link 716, the second rod connector 720, the second setscrew 728, and the second posterior cervical rod 732. FIG. 7 illustrates the adjustable occipital plate 700 with the rods 730, 732 being secured to the sliding links 714, 716, respectively. As can be further understood by one skilled in the art, there can be any number of posterior cervical rods secured to the adjustable occipital plate 700.

Prior to securing the cervical rod 730, a surgeon (or any other qualified user) may adjust the position and orientation of the sliding link 714 as well as the position and orientation of the cervical rod 730. As discussed above with regard to FIG. 2, the sliding links 714, 716 are preferably configured to rotate about lateral rods 710, 712, respectively, as well as (preferably), translate along the lateral rods 710, 712, respectively. The posterior cervical rods 730, 732 may also be configured to rotate about an axis that is substantially perpendicular to the top surface of the sliding links 714, 716. The cervical rods 730, 732 may also be configured to translate along channel 764 of the rod connectors 718, 720, respectively. The above-referenced translations and rotations allow a surgeon to custom-fit the occipital plate to a patient in accordance with patient's physiological characteristics and needs.

Referring back to FIG. 7, the fixation plate 702 includes three openings 704 (a, b, c). The openings 704 (a, b, c) are configured to accommodate cervical screws or any other type of screws or attachment/fastening devices (see FIG. 1). As can be understood by one skilled in the art, the fixation plate 702 may include at least one opening 704, where each opening 704 accommodates a screw. The fixation plate 702 along with the screw(s) allows attachment of the occipital plate 700 to bone in the neck region of the patient.

The structure of the posterior cervical rods 730, 732 may be similar to the structure of the cervical rods 130, 132 of FIGS. 1-2 discussed above.

Figure 5:
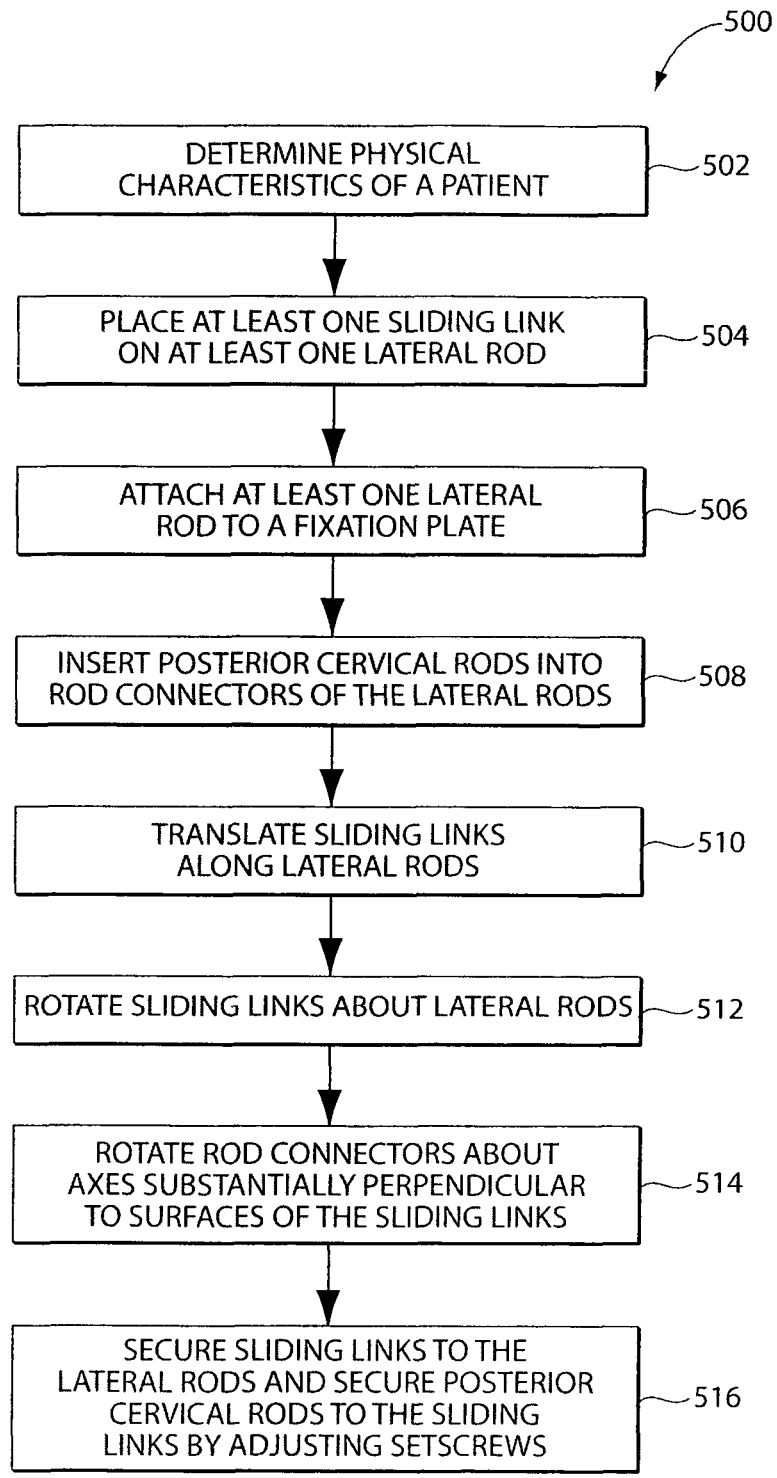
FIG. 5 is a flowchart illustrating an exemplary method of assembling and installing an adjustable occipital plate, according to the present invention.

An embodiment of an exemplary method 500 that may be used to assemble and adjust the occipital plate 100, shown in FIGS. 1-4, as well as, install it for the purposes of connecting patient's cranium and spine is illustrated in FIG. 5. As can be understood by one skilled in the art, the method 500 is equally applicable to the adjustable occipital plate 700 discussed above with regard to FIGS. 7-10.

Accordingly, in step 502, the surgeon (or any other qualified professional) examines the patient to determine patient's physical characteristics. Based on those characteristics, as illustrated in step 506, the surgeon selects a fixation plate 102 having a length, width, and thickness and including at least one opening 104 for insertion of at least one screw 106. The surgeon may then select a first end 110, a second end 112 and couple them to the selected fixation plate 102. Alternatively, the surgeon may select a lateral rod 108 and couple the rod to the fixation plate 102.

The first and second sliding links 114, 116 may be configured to be slidably coupled to the first and second ends 110, 112, respectively, prior to the ends being coupled to the fixation plate 102, as shown in step 504.

Steps 508-514 illustrate adjustment of the occipital plate 100 and as can be understood by one skilled in the art, can be performed in any order. Referring to steps 508-514, once the ends with the sliding links are coupled to the fixation plate 102, the surgeon may adjust the position of the sliding links by translating them along the respective ends. The surgeon may also adjust the links' angle of orientation by rotating them around the ends.

The surgeon may then insert the posterior cervical rods 130 and 132 into the respective rod connectors on the sliding links 114, 116. The rods 130, 132 may be inserted into the rod connectors prior to attachment of the sliding links to the ends 110, 112. Alternatively, the rods 130, 132 may be inserted into the rod connectors prior to adjustment of the sliding links. As can be understood by one skilled in the art, the insertion of rods 130, 132 (one or both) may be done at any time.

The rods 130, 132 may be then also rotated around axes that are substantially perpendicular to the surface of the respective sliding links. Once, the rods are set to a specific position, the rods may be secured to the sliding links using respective setscrews 126, 128. In an embodiment, the setscrews 126, 128 may be tightened using a tightening tool (such as a wrench, a screwdriver, allen-wrench, and the like). The tightening also secures the sliding links 114, 116 to the respective ends 110, 112.

As can be understood by one skilled in the art, the adjustment of the sliding links (including the cervical rods) may be performed when the fixation plate 102 is coupled to the patient's spine. Thus, a surgeon can install the occipital plate 100 into the patient' spine and then rotate and translate various components of the plate 100 and, after that, lock them into a static configuration. Thus, prior to installation, the occipital plate 100 may have a variety of motions about its various axes, but once it is installed, it may be secured in a static non-moving position. Alternatively, the occipital plate 100 may be adjusted outside of the patient's body, then locked into a static configuration, as illustrated in step 516. In another alternate embodiment, the occipital plate 100 may be partially secured, then installed into the patient, and locked into a static configuration.

As can be understood by one skilled in the art, other possible ways of adjusting and installing the occipital plate 100 are possible. Further, a static configuration of the occipital plate 100 is a configuration that may allow fewer motions (e.g., translations and rotations of at least one component of the plate 100) than its dynamic configuration, i.e., when none of the components are secured.

Referring back to FIG. 7, the adjustable occipital plate 700 is illustrated with the bone graft 1001 that is attached to the middle portion 707. The middle portion 707 may include a contoured extension or protrusion 1003 having a contoured edge 1004. In one embodiment, the contoured extension 1003 may be referred to as a graft containment mechanism, which may be configured to better secure the bone graft 1001 to the adjustable occipital plate 1001. The bone graft 1001 may be used to promote fusion at the occipito-cervical junction by creating a bridge between the occiput and the cervical lamina.

Figure 11:
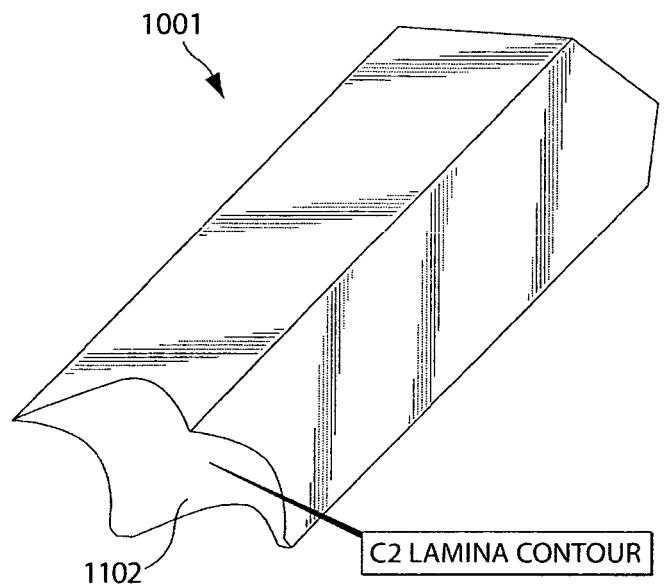
FIG. 11 is a perspective, cross-sectional view of a bone graft that can be used with an adjustable occipital plate illustrated in FIG. 7.
Figure 12:
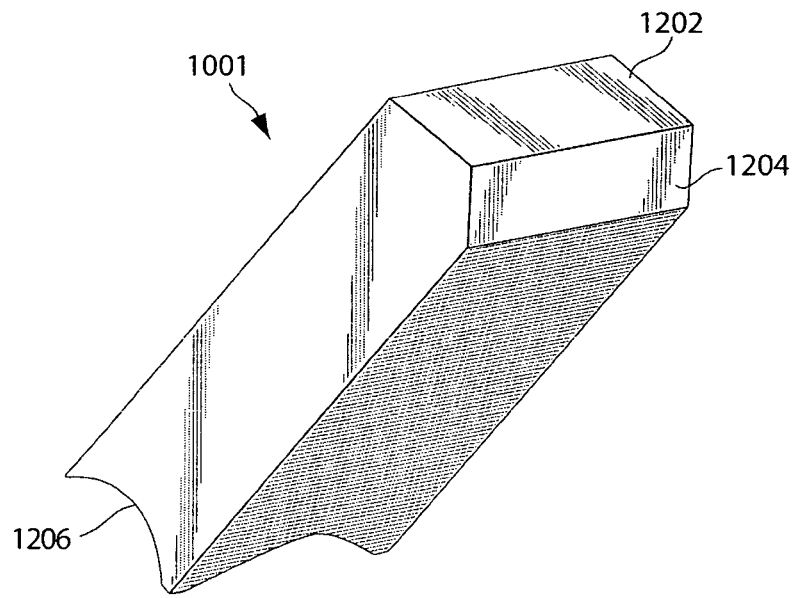
FIG. 12 is another perspective, cross-sectional view of the bone graft shown in FIG. 11.

The bone graft 1001 is further illustrated in FIGS. 11-12. In an embodiment, the bone graft 1001 may be multi-contoured having various shapes and edges to further promote fusion at the occipito-cervical junction. As illustrated, the bone graft 1001 is further configured to include a C2 lamina contour 1102 (shown as lamina contour 1206 in FIG. 12), a plate contact area 1202 (shown in FIG. 12), and a occiput contact area 1204 (shown in FIG. 12). The lamina contour 1102 (or 1206) or graft's distal end may be pre-contoured to adapt to posterior elements of the cervical spine (e.g., lamina, facets, spinous process). The plate contact area 1202 and the occiput contact area 1204 are pre-contoured to adapt to the adjustable occipital plate 700 and the occiput, respectively. In an embodiment, the bone graft 1001 may be manufactured from any biocompatible material, such as polyetheretherketone (PEEK), allograft tissue, titanium, and the like. As can be understood by one skilled in the art, the bone graft 1001 may have any shape, size, length, width, thickness, height, structure, or any other parameters.

Example embodiments of the methods and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

What is claimed:

1. An adjustable occipital plate, comprising:
a fixation plate;
at least one lateral rod configured to be coupled to said fixation plate;
at least one laterally sliding link that includes a round portion with an adjustable diameter configured to be coupled to said at least one lateral rod; and at least one posterior cervical rod configured to be coupled to said at least one laterally sliding link using at least one rod connector.

2. The adjustable occipital plate according to claim 1, further comprising at least one setscrew and at least one washer configured to couple said at least one posterior cervical rod, said at least one laterally sliding link and said at least one rod connector.

3. The adjustable occipital plate according to claim 1, wherein said fixation plate is configured to be coupled to two lateral rods.

4. The adjustable occipital plate according to claim 1, further comprising a first laterally sliding link and a second laterally sliding link.

5. The adjustable occipital plate according to claim 4, further comprising: a first rod connector configured to be coupled to said first laterally sliding link; and a second rod connector configured to be coupled to said second laterally sliding link.

6. The adjustable occipital plate according to claim 5, further comprising: a first posterior cervical rod configured to be coupled to said first rod connector; and a second posterior cervical rod configured to be coupled to said second rod connector.

7. The adjustable occipital plate according to claim 4, wherein said fixation plate is configured to be coupled between said first laterally sliding link and said second laterally sliding link.

8. The adjustable occipital plate according to claim 1, wherein said fixation plate is coupled to two lateral rods and the combination of said fixation plate and said two lateral rods is configured to form a curvature.

9. The adjustable occipital plate according to claim 1, wherein said at least one laterally sliding link is configured to translate along said at least one lateral rod.

10. The adjustable occipital plate according to claim 9, wherein said translation is a medial lateral translation.

11. An adjustable occipital plate, comprising:
a fixation plate;
at least one lateral rod configured to be coupled to said fixation plate;
at least one laterally sliding link that includes a round portion with an adjustable diameter configured to be coupled to said at least one lateral rod; and
at least one posterior cervical rod configured to be coupled to said at least one laterally sliding link using at least one rod connector,
wherein said at least one laterally sliding link is configured to rotate about said at least one lateral rod.

12. The adjustable occipital plate according to claim 1, wherein said at least one rod connector is configured to rotate about an axis substantially perpendicular to said laterally sliding link.

13. The adjustable occipital plate according to claim 1, wherein said fixation plate is configured to include at least one opening for receiving screws.

14. The adjustable occipital plate according to claim 13, wherein said fixation plate is configured to include two openings for receiving screws.

15. The adjustable occipital plate according to claim 13, wherein said fixation plate is configured to include three openings for receiving screws.

16. The adjustable occipital plate according to claim 1, further comprising a graft containment member.

17. The adjustable occipital plate according to claim 16, wherein said graft containment member is configured to secure a bone graft to the adjustable occipital plate.

18. The adjustable occipital plate according to claim 16, further comprising a bone graft.

19. The adjustable occipital plate according to claim 18, wherein the bone graft is selected from the group consisting of: PEEK, allograft tissue, and titanium.

20. The adjustable occipital plate according to claim 16, further comprising a bone graft and wherein a distal end of the bone graft is configured to correspond to one or more posterior elements of the cervical spine and a proximal end of the bone graft is configured to correspond to at least one of: a portion of the bone containment member and the occiput.

21. An adjustable occipital plate, comprising:
a fixation plate;
two lateral rods configured to be coupled to said fixation plate;
two laterally sliding links, that each includes a round portion with an adjustable diameter configured to be coupled to each of said two lateral rods; and
two posterior cervical rods, each is configured to be coupled to each of said two laterally sliding links using rod two connectors.

22. The adjustable occipital plate according to claim 21, further comprising two setscrews and two washers configured to couple said two posterior cervical rods, said two laterally sliding links and said two rod connectors.

23. The adjustable occipital plate according to claim 21, further comprising a first laterally sliding link and a second laterally sliding link.

24. The adjustable occipital plate according to claim 23, further comprising: a first rod connector configured to be coupled to said first laterally sliding link; and a second rod connector configured to be coupled to said second laterally sliding link.

25. The adjustable occipital plate according to claim 24, further comprising: a first posterior cervical rod configured to be coupled to said first rod connector; and a second posterior cervical rod configured to be coupled to said second rod connector.

26. The adjustable occipital plate according to claim 23, wherein said fixation plate is configured to be coupled between said first laterally sliding link and said second laterally sliding link.

27. The adjustable occipital plate according to claim 21, wherein said fixation plate further includes a curvature.

28. The adjustable occipital plate according to claim 21, wherein each of said two laterally sliding links is configured to translate along each of said two lateral rods.

29. The adjustable occipital plate according to claim 28, wherein said translation is a medial lateral translation.

30. The adjustable occipital plate according to claim 21, wherein each of said two laterally sliding links is configured to rotate about each of said two lateral rods.

31. The adjustable occipital plate according to claim 21, wherein each of said two rod connectors is configured to rotate about an axis substantially perpendicular to each of said two laterally sliding links.

32. The adjustable occipital plate according to claim 21, wherein said fixation plate is configured to include at least one opening for receiving screws.

33. The adjustable occipital plate according to claim 32, wherein said fixation plate is configured to include two openings for receiving screws.

34. The adjustable occipital plate according to claim 32, wherein said fixation plate is configured to include three openings for receiving screws.

35. The adjustable occipital plate according to claim 21, further comprising a graft containment member.

36. The adjustable occipital plate according to claim 35, further comprising a bone graft wherein said graft containment member is configured to secure the bone graft to the adjustable occipital plate.

37. The adjustable occipital plate according to claim 36, wherein said bone graft is manufactured from a biocompatible material.

38. The adjustable occipital plate according to claim 36, wherein a distal end of the bone graft is configured to correspond to one or more posterior elements of the cervical spine and a proximal end of the bone graft is configured to correspond to at least one of: a portion of the bone containment member and the occiput.

39. A method of assembling an adjustable occipital plate, comprising:
   providing a fixation plate and at least one lateral rod;
   slidably coupling at least one laterally sliding link to the at least one lateral rod;
   adjusting a diameter of a round portion of said at least one laterally sliding link;
   connecting the fixation plate to the at least one lateral rod; and
   coupling at least one posterior cervical rod to the at least one laterally sliding link using at least one rod connector.

40. The method according to claim 39, further comprising translating the at least one laterally sliding link along the at least one lateral rod.

41. The method according to claim 39, further comprising rotating the at least one laterally sliding link about the at least one lateral rod.

42. The method according to claim 39, further comprising rotating the at least one rod connector and the at least one posterior cervical rod around an axis substantially perpendicular to the at least one laterally sliding link.

43. The method according to claim 39, further comprising securing the at least one laterally sliding link to the at least one lateral rod.

44. The method according to claim 39, further comprising securing the at least one posterior cervical rod to the at least one laterally sliding link.

45. The method according to claim 39, further comprising installing the adjustable occipital plate into a patient.

* * * * *